United States Patent
Blancke et al.

(10) Patent No.: US 9,962,494 B2
(45) Date of Patent: May 8, 2018

(54) DRUG DELIVERY DEVICE WITH END OF DOSE FEEDBACK

(71) Applicant: SANOFI-AVENTIS DEUTSCHLAND GMBH, Frankfurt am Main (DE)

(72) Inventors: Stefan Blancke, Frankfurt am Main (DE); Axel Teucher, Frankfurt am Main (DE); Michael Jugl, Frankfurt am Main (DE); Christiane Schneider, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 256 days.

(21) Appl. No.: 15/036,528

(22) PCT Filed: Nov. 17, 2014

(86) PCT No.: PCT/EP2014/074702
§ 371 (c)(1),
(2) Date: May 13, 2016

(87) PCT Pub. No.: WO2015/074977
PCT Pub. Date: May 28, 2015

(65) Prior Publication Data
US 2016/0287803 A1  Oct. 6, 2016

Related U.S. Application Data

(60) Provisional application No. 61/907,473, filed on Nov. 22, 2013.

(30) Foreign Application Priority Data

Apr. 24, 2014  (EP) .................................. 14165746

(51) Int. Cl.
*A61M 5/315* (2006.01)
*A61M 5/24* (2006.01)
(Continued)

(52) U.S. Cl.
CPC .......... *A61M 5/31551* (2013.01); *A61M 5/24* (2013.01); *A61M 5/28* (2013.01);
(Continued)

(58) Field of Classification Search
CPC ............ A61M 5/20; A61M 5/24; A61M 5/28; A61M 5/315; A61M 5/31511;
(Continued)

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| EP | 0937471 | 8/1999 |
| EP | 0937476 | 8/1999 |

(Continued)

*Primary Examiner* — Bhisma Mehta
*Assistant Examiner* — James D Ponton
(74) *Attorney, Agent, or Firm* — McDonnell Boehnen Hulbert & Berghoff LLP

(57) ABSTRACT

A method and an assembly for providing a drug delivery device is presented. The assembly includes a housing and an end of dose feedback connection provides the user with an audible and/or tactile signal to indicate that the drug delivery is completed. A first section of the end of dose feedback connection is located on a distal portion of an inner sleeve and a second section of the end of dose feedback connection is located on the mid-body.

14 Claims, 5 Drawing Sheets

(51) Int. Cl.
*A61M 5/28* (2006.01)
*A61M 5/31* (2006.01)

(52) U.S. Cl.
CPC ...... *A61M 5/3157* (2013.01); *A61M 5/31575* (2013.01); *A61M 5/31578* (2013.01); *A61M 5/31585* (2013.01); *A61M 5/3146* (2013.01); *A61M 5/31558* (2013.01); *A61M 5/31561* (2013.01); *A61M 5/31593* (2013.01); *A61M 2005/3104* (2013.01); *A61M 2205/581* (2013.01); *A61M 2205/582* (2013.01)

(58) Field of Classification Search
CPC ............ A61M 5/31565; A61M 5/3157; A61M 5/31575; A61M 5/31576; A61M 5/31578; A61M 5/31583; A61M 5/31558; A61M 5/31561; A61M 5/31593; A61M 5/31551; A61M 2205/581; A61M 2205/582
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2006/0206057 A1* | 9/2006 | DeRuntz | A61M 5/31551 604/224 |
| 2009/0275916 A1 | 11/2009 | Harms et al. | |

FOREIGN PATENT DOCUMENTS

| | | |
|---|---|---|
| EP | 2891503 | 7/2015 |
| WO | 99/38554 | 8/1999 |
| WO | 01/10484 | 2/2001 |
| WO | 2005/018721 | 3/2005 |
| WO | 2014/040929 | 3/2014 |
| WO | 2014/166908 | 10/2014 |
| WO | 2014/166922 | 10/2014 |
| WO | 2015/007821 | 1/2015 |

\* cited by examiner

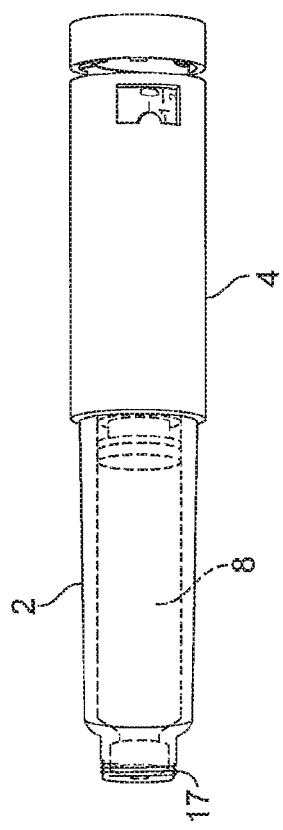
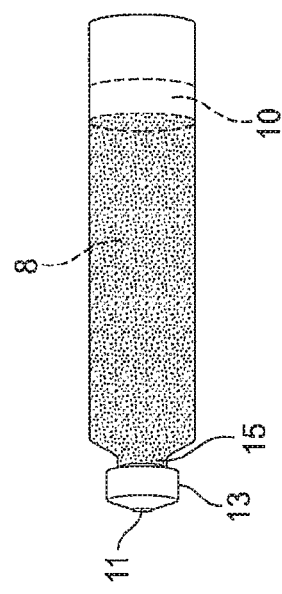
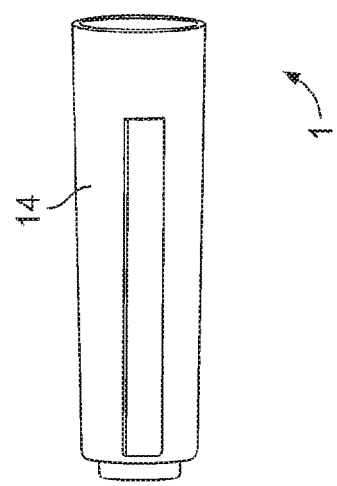
FIG. 1
FIG. 2

DRUG DELIVERY DEVICE WITH END OF DOSE FEEDBACK

CROSS REFERENCE TO RELATED APPLICATIONS

The present application is a U.S. National Phase Application pursuant to 35 U.S.C. § 371 of International Application No. PCT/EP2014/074702 filed Nov. 17, 2014, which claims priority to U.S. Provisional Patent Application No. 61/907,473 filed Nov. 22, 2013 and European Patent Application No. 14165746.0, filed Apr. 24, 2014. The entire disclosure contents of these applications are herewith incorporated by reference into the present application.

TECHNICAL FIELD

The present patent application is generally directed to drug delivery devices, such as pen-type injection devices, and preferably to the dose setting and/or dose delivery mechanisms for such drug delivery devices. Particularly, the present disclosure relates to an assembly for such drug delivery devices and to drug delivery devices comprising such assemblies. Such devices provide for self-administration of medicinal product from a multi-dose cartridge and permit a user to set the delivery dose. The present application may find application in both disposable and reusable type drug delivery devices. However, aspects of the invention may be equally applicable in other scenarios as well.

BACKGROUND

Pen type drug delivery devices have application where regular injection by persons without formal medical training occurs. This is increasingly common among patients having diabetes where self-treatment enables such patients to conduct effective management of their disease. Diabetes has been shown to cause certain problems. For example, people with diabetes can get high blood pressure, kidney disease, nerve damage, heart disease, and even in certain circumstances blindness. The damage caused by these problems may occur in patients whose blood sugar has been out of control for years. Keeping blood sugar under control, by way of effective insulin administration, is one method that can help prevent this damage from occurring.

In addition, people with diabetes can go into "diabetic coma" if their blood sugar is too high. They can also develop blood sugar that is too low (i.e, hypoglycemia) if they don't get enough food, or they exercise too much without adjusting insulin or food. Both diabetic coma and hypoglycemia can be very serious, and even fatal, if not treated quickly. Closely watching blood sugar, being aware of the early signs and symptoms of blood sugar that is too high or too low, and treating those conditions early can prevent these problems from becoming too serious.

Pen type drug delivery devices have been designed and developed to help patients suffering from diabetes and other disease states so as to prevent such problems from occurring. The circumstances identified above highlight a number of design considerations and criteria for drug delivery devices, especially those that may be used to treat diabetes. As just one example, one requirement is that the drug delivery device must be robust in construction. The drug delivery device must also be easy to use both in terms of the drug delivery device manipulation and understanding of the device's operation. Diabetics, for instance, have to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

Generally, pen type injection devices include a cartridge having a slidable piston and containing a multi-dose quantity of liquid medication. A lead screw extending from the dose setting mechanism of the injector pen is movable in a forward (i.e., distal direction) to advance the piston within the cartridge in such a manner as to dispense the contained medication from an outlet at the opposite cartridge end, typically through a needle that penetrates a stopper or septum at that opposite end. In disposable or prefilled pens where the cartridge is permanently sealed within the pen housing, after a pen has been utilized to exhaust the supply of medication within the cartridge, the entire pen is then discarded. In reusable pens, after a pen has been utilized to exhaust the supply of medication within the cartridge, the pen is disassembled to allow replacement of the spent cartridge with a fresh cartridge, and then the pen is reassembled for its subsequent use.

A number of pen type injection devices are commercially available and unfortunately a number of those devices suffer from one or more design flaws that may result in the improper use of the injection device or the delivery of an inaccurate dosing of the medicament. Inaccurate dose setting could lead to fatal results. Other design flaws allow the possibility that a counterfeiter can dissemble a disposable pen and insert bogus medicament cartridge. This pen is then reassembled and sold as new. In some cases, the initially designed device does not provide feedback to a user during dispensing of the preset dose or at the completion of the dose. For the users who are visually and/or hearing impaired the ability to receive audible or tactile feedback is very important in order that the user hears or feels that the preset dose is being delivered and importantly that the injection is completed. Knowledge of the completion of the injection is very important to ensure a proper delivery of medicament is performed because users are taught to leave the injection needle in the skin for 10 seconds at the end of dosing to make sure all the medicament is delivered. Without such feedback features the risk of an improper injection being performed or under dosing is greatly increased, especially if the user dose not know when to begin the 10 second countdown. Such design flaws may not be realized when a pen is first commercialized and may only become apparent after the injection device has been in commercial use by patients for an extended period of time. As such, there exists a need to evaluate existing pen designs to identify the design flaws and then take corrective action, which typically would include redesigning certain original mechanisms within the injection device.

One such pen injector lending itself to design improvements is described in WO 2005/018721. The following describes a number of such design flaws and presents corrective solutions which are, inter alia, suitable to eliminate these flaws.

SUMMARY

Most, if not all, pen injection type devices are designed to allow for self-administration of medicament in preset doses by the patient suffering from one or more disease state. Depending on treatment regime set by the caregiver, a patient may have to perform self injections several times a day. For this reason, pen type devices must be designed for all types of users, including the very young and the very old who may suffer from poor vision or hearing or manual dexterity. It is imperative therefore that the design of the injection device provide some type of feedback system to indicate to the user/patient that the injection is progressing correctly and that the injection is complete. For example, if there is no end of dose feedback signal provided, the user may inadvertently stop the injection process before the required full dose is delivered. This of course would lead to under dosing, which in some disease states could be very dangerous to the user.

It is an object of the present disclosure to provide an assembly for a drug delivery device, which facilitates provision of novel, preferably an improved, drug delivery device.

This object is achieved by the subject matter of the independent claim. Advantageous refinements and developments are subject matter of the dependent claims.

Features herein which are disclosed in conjunction with a drug delivery device should be regarded as also being disclosed for the assembly for the drug delivery device.

According to an aspect, the drug delivery device comprises a housing. The drug delivery device further comprises a lead screw having a distal end and a proximal end. The lead screw preferably includes a threaded shaft. The drug delivery device further comprises a drive nut which is threadedly engaged with the lead screw and screwable along the lead screw. Particularly, the drive nut is threadedly with and screwable along the threaded shaft. Still further, the drug delivery device comprises an inner sleeve which is axially movable and rotatably fixed relative to the housing. Thus, expediently, axial movement of the inner sleeve with respect to the housing is permitted whereas rotational movement of the inner sleeve relative to the housing is prevented. Furthermore, the drive nut is axially fixed to the inner sleeve. Expediently, the drive nut may rotate with respect to the inner sleeve while being axially fixed thereto. The inner sleeve also has a portion, preferably a distal portion, which contains a first section of an end of dose feedback connection. The drug delivery device also comprises a second section of the end of dose feedback connection which is provided axially fixed and preferably rotatably fixed within the housing. Consequently, the second section of the end of dose feedback connection preferably does not rotate and does not move axially within the housing. The second section of the end of dose feedback connection may be formed integrally with the housing or in a separate body part which is, for example, rotatably and axially fixed within the housing.

The drug delivery device is configured such that, during dose setting or for dose setting, the drive nut is screwed along the lead screw, in particular along the threaded shaft thereof. When doing so, the drive nut may carry the inner sleeve with it, as the drive nut is axially fixed to the inner sleeve. The device is further configured such that, during dose delivery or for dose delivery, the inner sleeve is advanced without rotation, particularly in the distal direction and/or with respect to the housing, to axially advance the drive nut and thereby the lead screw. During dose delivery the drive nut preferably does not rotate.

During dose setting, the drive nut and, consequently, the inner sleeve may be displaced in the proximal direction from an initial position, which may be a home position or a zero dose position, towards a dose set position. The distance of the axial displacement of the drive nut relative to the lead screw may determine the size of the dose which should be delivered later on during dose delivery. During dose delivery, the drive nut and, together with it, the inner sleeve are moved from the dose set position back towards the initial position. When the initial position has been reached again, dose deliver has been completed.

The proposed drug delivery device has a first section of an end of dose feedback connection and a second section of an end of dose feedback connection. These sections are preferably configured to interact to provide some kind of signal or feedback to a user when they interact, e.g. when a connection between these sections is established. In this way, an end of dose feedback signal may be provided to the user. The proposed drug delivery device utilizes sections of an end of dose feedback connection which are reliably positioned within the drug delivery device. Particularly, the first section of the end of dose feedback connection is provided on the inner sleeve which is prevented from rotation. As the second section of the end of dose feedback connection is axially fixed within the housing, during dose setting the first section is moved proximally with respect to the second section and back towards the first section during dose delivery. As this movement is a pure axial movement due to rotation of the inner sleeve being prevented, and as the second section is axially fixed, the connection can be established reliably, as a movement of the second section in that direction in which the first section moves axially is prevented and the connection can be established reliably. Consequently, a relative movement which is required to bring the two sections into cooperation requires, preferably only, axial movement of the inner sleeve. Axial movement is, of course, very reliable and rotational movement components do not have to be taken into account when the end of dose feedback connection is established to provide an end of dose feedback to the user.

When the connection between the first and second section of the end of dose feedback connection is established, an end of the dose delivery may be signaled to the user in a sensory manner such that it can be recognized by the user. Consequently, in the proposed drug delivery device, the user can be sure that, if he perceives the end of dose feedback, dose delivery has been completed and no uncertainty exists in this regard.

In an embodiment, the drug delivery device comprises a cartridge. The cartridge may comprise a movable piston at one end and an outlet at the other end. The piston may be movable towards the outlet when the lead screw is moved during dose delivery. The cartridge may comprise a fluid, which may contain a medicinal product. When the piston is moved towards the outlet, fluid may be dispensed from the outlet of the cartridge. The piston may be engageable by the lead screw, particularly by a bearing foot thereof, to be advanced towards said outlet when the lead screw is moved, e.g. moved distally.

In an embodiment, the first section of the end of dose connection and the second section of the end of dose connection are configured to cooperate mechanically. The sections are expediently configured to cooperate mechanically such that, preferably due to this cooperation, a sensory indication or feedback is produced, for example an audible or tactile signal. The indication or feedback may indicate that dose delivery has been completed. Thus, a signal or feedback is provided which signals to the user that dose delivery has been completed due to a mechanical cooperation of the sections. An audible and/or a tactile signal has the advantage over a visual signal that the eyes of the user do not have to locate a display. Rather, the signal can be perceived by the user via the ears in case of an audible signal or the hand which already holds the drug delivery device in case of a tactile signal.

In an embodiment, the lead screw is rotatably fixed during dose setting and/or during dose delivery. Consequently, rotational movement of the lead screw during dose setting or during dose delivery may be prevented as it is rotatably fixed. Furthermore, the lead screw is expediently axially movable in a distal direction relative to the housing. The lead screw may include the threaded shaft and a bearing foot connected to the distal end of the lead screw or forming the distal end of the lead screw.

In an embodiment, the drug delivery device comprises a number sleeve. The inner sleeve may be engaged, particularly threadedly engaged, with the number sleeve. In this way, rotational movement of the number sleeve may be converted into axial movement of the inner sleeve as rotational movement of the inner sleeve is prevented. The number sleeve may be threadedly engaged with the housing, particularly to be screwable relative to the housing. Consequently, rotation of the number sleeve with respect to the housing may result in an according axial displacement of the number sleeve defined by the threaded engagement of the number sleeve to the housing.

In an embodiment, the threading, e.g. the thread which defines the threaded engagement, between drive nut and lead screw is of a third lead, the threading of the inner sleeve to the number sleeve is of a second lead and the threading of the number sleeve to the housing is of a first lead. An arbitrary one of these leads may be different from an arbitrary one of the remaining leads. Preferably, any arbitrarily selected pair of these leads has two different leads. The first lead is preferably greater than the second lead and/or the third lead. The third lead is preferably smaller than the second lead. The sum of the second and third lead may equal the first lead.

The specific leads of the threads which define the threaded engagement of the drive nut and the lead screw, the inner sleeve and the number sleeve or, where applicable the number sleeve and the housing, facilitate that the drive nut and the inner sleeve are only displaced by a smaller extent axially than is the number sleeve. Consequently, the movement which the inner sleeve performs relative to the second section of the end of dose feedback connection is relative small particularly as compared to the one of the number sleeve. Smaller distances are more reliable than movements over greater distances. Thus, the end of dose feedback connection can be established more reliably as compared to an end of dose feedback connection which requires a greater travel distance of the associated parts before being established.

In an embodiment, the drug delivery device comprises a dial link. The dial link may be connected with the drive nut. The dial link may be axially movable relative to the drive nut. The dial link may be rotatably fixed relative to the drive nut. Consequently, relative rotational movement between drive nut and dial link may be prevented. The drug delivery device may be designed such that there are at least two different axial arrangements of number sleeve and dial link. Between these arrangements it may be switched via relative movements being performed between dial link and number sleeve. When the dial link and number sleeve are in a first axial arrangement, the dial link may be rotatably fixed with the number sleeve. Consequently, in the first axial arrangement, relative rotation between dial link and number sleeve may be prevented. In a second axial arrangement the number sleeve may be rotatable relative to the dial link. A clutch may be provided which couples number sleeve and dial link rotationally in the first axial arrangement, the clutch being released in the second axial arrangement. In the second axial arrangement, the dial link may be coupled to the inner sleeve by means of a coupling engagement in order to prevent rotation of the dial link relative to the inner sleeve and, as the inner sleeve is prevented from rotation with respect to the housing. Number sleeve and dial link may be in the first axial arrangement during dose setting and in the second axial arrangement during dose delivery.

When the dial link and the number sleeve are in the first axial arrangement, i.e. during dose setting, a screwing motion of the dial link and the number sleeve relative to the housing may screw the dial link and the number sleeve by a first axial distance from a home position. This screwing motion of the dial link screws the drive nut along the threaded shaft of the lead screw by a second axial distance that is different than the first axial distance. The difference between first and second axial distance may result from the different leads of the associated threadings.

During dose delivery, the dial link and the number sleeve are in the second axial arrangement. Thus, a screwing motion of the number sleeve relative to the housing moves the number sleeve back towards the home position. During the movement of the number sleeve towards the home position or due to the movement of the number sleeve towards the home position, the inner sleeve may be advanced without rotation in the distal direction in order to axially advance the drive nut that is axially fixed to the inner sleeve and thereby the lead screw. When doing so, the movable piston within the cartridge may be advanced in the distal direction in order to dispense fluid from the cartridge outlet.

In an embodiment, the drug delivery device comprises a body part. The body part may contain or comprise the second section of the end of dose feedback connection. The body part may be axially, and preferably rotatably, fixed inside of the housing. Consequently, the body part may not be moved axially and/or may not be rotated with respect to the housing. The inner sleeve may be axially movable and rotatably fixed relative to the body part. Consequently, the inner sleeve may move axially relative to the body part but may not rotate relative to the body part. The inner sleeve may be rotatably fixed relative to the body part by at least one lug of the body part that slidably fits within at least one slot formed in the inner sleeve. The body part may include tabs that slidably fit within keyways in the lead screw to prevent rotation of the lead screw within the housing. Further, the body part may be a mid-body. The mid-body may be positioned in a central portion of the device. The mid-body may be positioned close to the distal end of the lead screw when the lead screw is in its original position and no drug has been dispensed yet from the drug delivery device In an embodiment, the drive nut is rotatable with respect to the inner sleeve. Preferably, the drive nut rotates with respect to the inner sleeve during dose setting. Rotation of the drive nut with respect to the inner sleeve is expediently prevented during dose delivery. The drive nut and the inner sleeve may comprise one or more corresponding feedback features which are configured to cooperate mechanically such that, when the drive nut rotates relative to the inner sleeve, an audible and/or tactile feedback is generated. For doing so, the drive nut may comprise one or more first feedback features and the inner sleeve may comprise one or more second feedback features. The first and second feedback features may be provided to establish or form a clicker mechanism, particularly a dose setting clicker mechanism, of the drug delivery device.

In an embodiment, the first section of the end of dose feedback connection and the feedback feature of the inner sleeve are arranged in the same portion of the inner sleeve, for example in the distal portion of the inner sleeve. Consequently, the end of dose feedback and the feedback generated by the feedback features may originate from the same portion of the device. Thus, an end of dose feedback and a dose setting feedback may be generated such that these feedbacks may be perceived by the user as originating from the same region, i.e. that region in which the dose setting feedback is generated right at the beginning of dose setting. This increases the user's confidence regarding the reliable operation of the device. The first section of the end of dose connection may be provided on an outer surface of the inner sleeve. The feedback feature of the inner sleeve may be provided on an inner surface of the inner sleeve. Alternatively, the surface of the inner sleeve may comprise one or more openings or cut-outs to define the feedback feature of the inner sleeve. The respective feedback feature of the inner sleeve may be a flexible or resilient finger or arm or a flexible portion. The respective feedback feature of the drive nut may be a tooth.

In an embodiment, the first section of the end of dose feedback connection and the second section of the end of dose feedback connection are configured to establish a releasable connection or engagement. The first and the second section may be connected or engaged before dose setting is commenced. The connection or engagement between the first and second section may be released during dose setting, preferably right at the beginning of dose setting. The connection between the first and second sections may be re-established at the end of dose delivery. Expediently, the sections are designed such a feedback is generated at least at the end of dose delivery. Preferably, no feedback, a substantially lesser feedback or a substantially different feedback is generated when the connection is released as compared to when it is re-established. Consequently, the user may distinguish an end of dose feedback from an operating noise generated right at the beginning of dose setting. This may be realized, for example, by appropriate shaping of the first and second sections, such as a ramp shape or similar shapes described furthermore below and in the exemplary embodiments. The connection or engagement between the first and second section of the end of dose feedback connection may be a snap fit connection or engagement.

The connection between the first and second section may be established at a zero dose setting, particularly when a dose of the size zero is set, i.e. when the device is in a ready to set a dose state. Thus, the first and second sections of the end of dose feedback section may cooperate at a zero dose setting to form a releasable snap fit engagement or connection. The first and second sections of the end of dose feedback connections may be configured to generate an audible sound when the sections cooperate to form the releasable snap fit connection or engagement. Consequently, when the snap fit connection or engagement is being established, the audible sound may be generated.

In an embodiment, the first and second sections of the end of dose feedback connection are configured to generate a tactile sensation perceptible to a user holding the drug delivery device when the sections cooperate to form the releasable snap-fit connection or engagement.

In an embodiment, the first section of the end of dose feedback connection is a flexible click arm. In an embodiment, the second section of the end of dose feedback connection is a ramped detent, a hole, or an indentation. The ramped detent, the hole or the indentation may be configured to generate an audible sound when connected with the click arm.

In an embodiment, the first section of the end of dose feedback connection comprises at least two click arms. The second section of the end of dose feedback connection may comprise at least two ramped detents or two holes or two indentations. The detents, holes or indentations may be radially or diametrically positioned on the body part to cooperate and engage the at least two click arms, particularly simultaneously and/or at a zero dose setting. In this way, audible and/or tactile signals may be generated to a user holding the drug delivery device.

Of course, the click arm(s) could also be comprised by the second section of the end of dose feedback connection, whereas the first section of the end of dose feedback connection could comprise the ramped detent(s), the hole(s) or the indentation(s).

A physical examination of the commercial pen injection device that is generally described in WO 2005/018721 shows that a feedback signal is only provided during the setting of a dose and not during dose delivery or at the completion of the dose. To solve this problem, the present disclosure proposed a modified design to enable an end of dose audible feedback signal in the form of a loud "CLICK" when the set dose has been fully delivered or injected as disclosed above and below. One such method for modifying the pen injection device described in the WO 2005/018721 publication includes redesigning the mid-body and inner sleeve components such that they interact to generate a loud click noise to occur when the full dose has been completely injected. One way to achieve this feedback feature is to include a click arm on the mid-body component of the device that snaps into a ramp detent or into a hole or indentation, which is added to the distal portion of the inner sleeve component at the moment the injection is complete. As the inner sleeve is driven distally into the mid-body during the injection, the click arm will ride up and over a detent ramp or will snap into a hole/indentation on the inner sleeve. The click arm will snap into a detent or hole in the inner sleeve simultaneously with the end of stroke completing the injection. This snapping will generate a loud audible "CLICK" that is not only heard by the user, but is also felt as a result of the tactile vibration caused by the snapping of the click arm into the detent or opening.

The pen type delivery device drug including the above described design improvement includes a housing, a lead screw having a threaded shaft is rotatably or rotationally fixed during dose setting and injecting that only moves axially in a distal direction relative to the housing during dose administration and is always prevented from moving proximally. The device also has a fluid container or cartridge defining a medicine-filled reservoir with a movable piston at one end and an outlet at the other end, where the piston is engaged by a bearing connected to the distal end of the lead screw. The piston is advanced toward the outlet or distal end of the cartridge when the lead screw is moved distally during dose administration.

A drive nut is threadedly engaged with the threads on the lead screw and can rotate and move proximally relative to the lead screw and housing during dose setting. A number sleeve is threadedly engaged with the housing and is screwed outwardly in the proximal direction relative to the housing during dose setting. A dial link is slidably and rotationally engaged with the drive nut and is axially movable and rotatably or rotationally fixed relative to the drive nut. The dial link is rotatably or rotationally fixed with the number sleeve through a clutch when the dial link and number sleeve are in a first axial arrangement and when in a second axial position the clutch, and hence the number sleeve, are disengaged from the dial link and the dial link becomes rotatable relative to the number sleeve. An inner sleeve is threadedly engaged with the number sleeve, were the inner sleeve is axially movable but rotatably or rotationally fixed relative to the housing. During dose setting, the dial link and the number sleeve are in the first axial arrangement, whereby a screwing motion of the dose knob that is connected to the dial link and number sleeve relative to the housing screws the dial link and the number sleeve a first axial distance from a home position causing the number sleeve to extend in the proximal direction outwardly from the housing or body of the device. The screwing motion of the dial link screws the drive nut along the lead screw threaded shaft a second axial distance different than the first axial distance.

During dose dispensing, the dial link and the number sleeve element are in the second axial arrangement, whereby a screwing motion of the number sleeve relative to the housing back or inward toward the home position advances the inner sleeve without rotation in the distal direction to axially advance the drive nut and thereby the lead screw and the fluid container piston to dispense medicine from the outlet. The pen injector disclosed herein can be provided with a mechanical advantage that makes it easier for the user to push the dose knob during the dispensing of medication, which mechanical advantage can be very high and conveniently selected by the manufacturer during apparatus design. This mechanical advantage allows the number sleeve to travel a greater axial distance than the lead screw it advances, thus allowing for small doses to be delivered.

In the following text, a set of advantageous aspects is described. The aspects are numbered to facilitate referencing features of one aspect in other aspects. Features from the aspects are not only relevant in connection with the specific aspects they relate to but are also of relevance on their own.

1. A drug delivery device comprising:

a housing;

a lead screw having a distal end and a proximal end that is rotatably fixed during dose setting and dose delivery and axially movable in a distal direction relative to the housing, the lead screw including a threaded shaft and a bearing foot connected to the distal end;

a cartridge with a movable piston at one end and an outlet at the other end, the piston engagable by the lead screw bearing foot to be advanced toward said outlet when the lead screw is moved distally;

a drive nut threadedly engaged and screwable along the lead screw threaded shaft;

a number sleeve threadedly engaged with the housing to be screwable relative to the housing;

a dial link connected with the drive nut and axially movable and rotatably fixed relative to the drive nut, the dial link rotatably fixed with number sleeve when the dial link and number sleeve are in a first axial arrangement, the number sleeve rotatable relative to the dial link when the dial link and number sleeve are in a second axial arrangement;

an inner sleeve threadedly engaged with the number sleeve, the inner sleeve axially movable and rotatably fixed relative to the housing and having a distal portion containing a first section of an end of dose feedback connection;

a mid-body axially fixed inside of the housing, the mid-body including tabs that slidably fit within keyways in the lead screw to prevent rotation of the lead screw within the housing and contains a second section of the end of dose feedback connection, wherein the inner sleeve is axially movable and rotatably fixed relative to the mid-body by at least one lug of the mid-body that slidably fits within at least one slot formed in the inner sleeve; and wherein the threading of number sleeve to the housing is of a first lead, the threading of the inner sleeve to the number sleeve is of a second lead, and the threading of the lead screw threaded shaft is of a third lead, and the first lead, the second lead and the third lead are not equal;

wherein during dose setting, the dial link and the number sleeve are in the first axial arrangement, whereby a screwing motion of dial link and number sleeve relative to the housing screws the dial link and the number sleeve a first axial distance from a home position, which screwing motion of dial link screws said drive nut along the lead screw threaded shaft a second axial distance that is different than the first axial distance; and wherein during dose delivery, the dial link and number sleeve are in said second axial arrangement, whereby a screwing motion of the number sleeve relative to the housing back toward the home position advances the inner sleeve without rotation in the distal direction to axially advance the drive nut that is axially fixed to the inner sleeve and thereby the lead screw and the movable piston to dispense fluid from the cartridge outlet.

2. The drug delivery device of aspect 1 where the first and second sections of the end of dose connection cooperate at a zero dose setting to form a releasable snap fit engagement.

3. The drug delivery device of aspect 1 where the first and second sections of the end of dose connection are configured to generate an audible sound when the sections cooperate to form a releasable snap fit connection.

4. The drug delivery device of aspect 1 where the first and second sections of the end of dose connection are configured to generate a tactile sensation perceptible to a user holding the drug delivery device when the sections cooperate to form a releasable snap fit connection.

5. The drug delivery device of aspect 1 where the first section of the end of dose connection is a flexible click arm and the second section of the end of dose connection is a ramped detent or hole or indentation configured to generate an audible sound when connected with the click arm.

6. The drug delivery device of aspect 1 where the first section of the end of dose connection comprises at least two click arms and the second section of the end of dose connection comprises at least two ramped detents or two holes or two indentations radially positioned on the mid-body to cooperate and engage the at least two click arms simultaneously at a zero dose setting to generate audible and tactile signals to a user holding the drug delivery device.

The above described advantages as well as other advantages of the various aspects and embodiments of our improved drug delivery device, and the manner of attaining them, will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 is an illustration of one embodiment of the present invention showing the assembled pen type medication dispensing apparatus where the cap has been removed to reveal the cartridge container or holder affixed to the dose setting mechanism;

FIG. 2 is a close up view of the cartridge container and the pen needle that is attached to the cartridge container for injection of the medicament;

Figure 3:
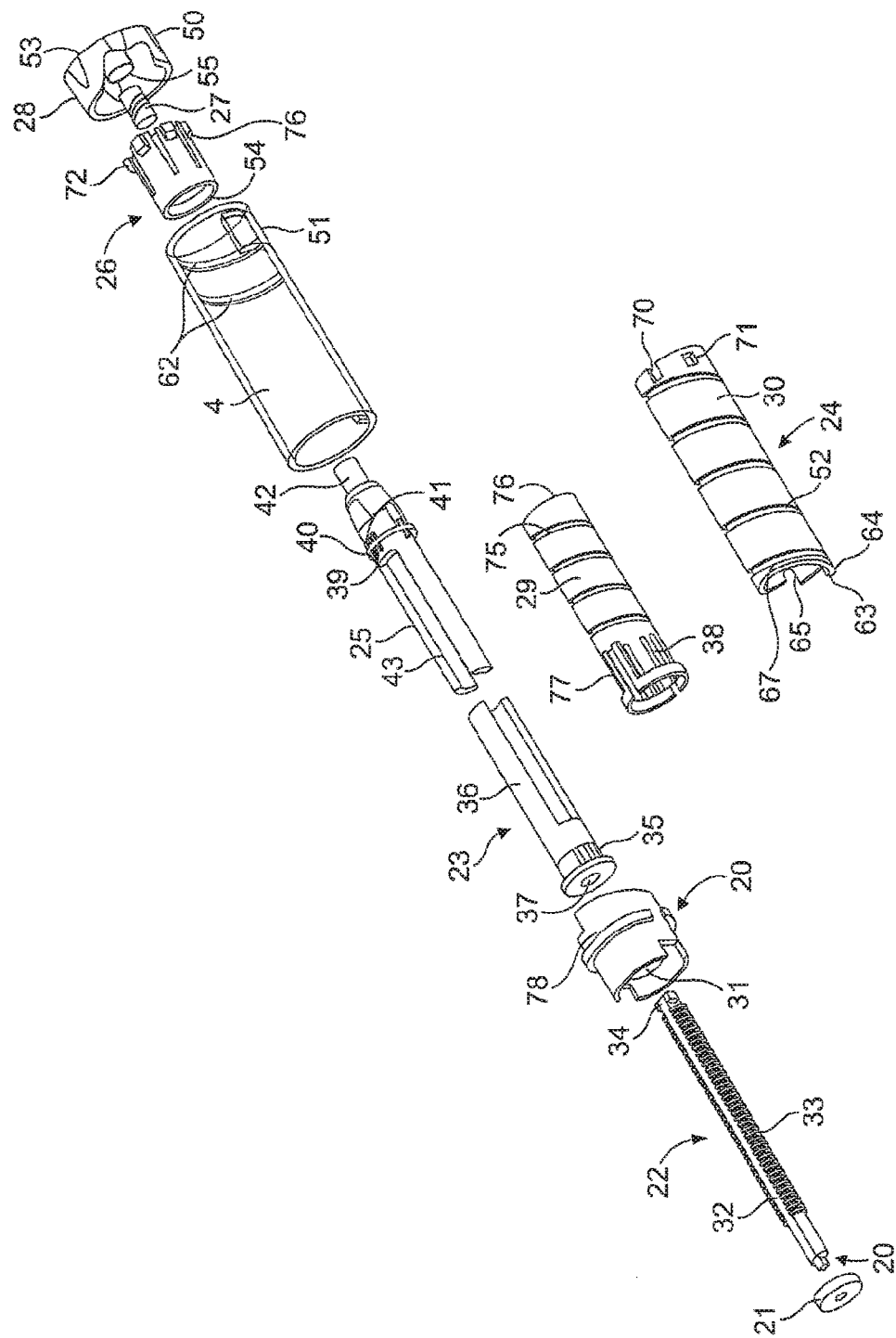
FIG. 3 is an exploded view of the embodiment from FIG. 1 showing each of the individual parts arranged relative to each other as they exist in the fully assembled device.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION

Referring first to FIGS. 1 to 3, there is shown a drug delivery device 1 as an injector pen, which pen has an elongated, substantially writing instrument-like form, although other forms are within the scope of the invention. In other words, the drug delivery device 1 may be a pen-type device. The drug delivery device 1 comprises a housing having a cartridge holder 2, and main (exterior) body or housing 4.

The drug delivery device 1 and the housing have a distal end and a proximal end. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end and the proximal end are spaced apart from one another in the direction of an axis. The axis may be the longitudinal axis or rotational axis of the device 1.

The proximal end of the cartridge holder 2 and the distal end of the main housing 4 are secured together by appropriate retaining features depending on whether the pen injector is designed as a reusable device or as a disposable device. In the latter case, the retaining feature would be permanent using the connection means described below. If the device is reusable, the retaining meaning would be a screw type connection, a Luerlok, snap fit, bayonet, or the like type or combination of fittings that allow the user to easily disassemble the device to replace the empty cartridge with a fresh new cartridge. In this illustrated arrangement, the cartridge holder 2 is secured within the proximal end of the main body 4.

A cartridge 8 from which a number of doses of a medicinal product may be dispensed is provided in the cartridge holder 2. Preferably, the cartridge contains a type of medicament that must be administered often, such as once or more times a day. One such medicament is insulin. A piston 10 shown in FIG. 2 is initially retained in the proximal end of the cartridge and as each injection is completed gradually moves distally to the empty cartridge position. A removable cap 14 is releasably retained connected to the main body 4 covering the cartridge holder 2. The dose setting mechanism of the drug delivery device 1 illustrated in FIGS. 1 to 3 may be utilized as either for a disposable or reusable drug delivery device. Where the drug delivery device 1 comprises a disposable drug delivery device, the cartridge cannot be removed from the device without destroying the device. In a disposable device, the proximal end of the cartridge holder 2 can be fixedly mounted or secured, via adhesives, ultrasonic welding or in another suitable manner, to the dose setting mechanism housing when the injector pen is assembled by the manufacturer. Alternatively, where the drug delivery device 1 comprises a reusable drug delivery device, the cartridge 8 is removable and may be removed from the device without destroying the device. In the drug delivery device 1 illustrated in FIGS. 1-3, the device is illustrated as a disposable drug delivery device. However, those of ordinary skill in the art will recognize that the dose setting mechanism could also be used on reusable drug delivery devices as well, while in the case of a reusable pen, wherein the cartridge holder may be reusable, such that the proximal end can be removably mounted or secured, for example via a threaded, bayonet, or snap fit connection, to a reusable dose setting mechanism having a resettable lead screw.

The removable or replaceable cap 14 is used to cover the cartridge holder 2 extending from the main housing 4. Preferably, the outer dimensions of the replaceable cap 14 are similar to or identical to the outer dimensions of the main housing 4 so as to provide an impression of a unitary whole part when the replaceable cap 14 is in position covering the cartridge holder 2. In use, the removable cap 14 is removed and a pen needle assembly 16 comprising a double-ended needle 16 mounted in a hub may be screwed or pushed onto the distal end of the cartridge holder or alternatively may be snapped onto this distal end.

Cartridge 8 is of conventional design and defines a medicine-filled reservoir that is closed at its proximal end by the piston 10 that is axially slidably and sealably engaged with the cartridge interior wall to hold the fluid medication within the reservoir. The distal, outlet end of the cartridge reservoir is sealed by a septum 11 held by a cap 13 that is secured to a stepped-down diameter neck portion 15 of the cartridge. When pen needle assembly 16 is mounted on the distal end of the cartridge holder 2, the proximal point of injection needle 16 passes through a central opening in the distal end of the cartridge holder 2, an opening in cap 13, and penetrates cartridge septum 11 to provide a fluid flow outlet by which medicine within the cartridge reservoir can be dispensed from the distal needle tip during operations of injector pen 1. The fluid medicine cartridge shown and described above is illustrative and not intended to be limiting as other constructions may be employed within the scope of this invention.

Main body 4 of injector pen 1 houses an axially advanceable lead screw 22, a drive nut 23, a inner sleeve 29, a dial link 25, a number sleeve 24, a clutch 26, and a spring 27, such as a compression or biasing spring. A dose knob 28 is connected to the dial link 25 and is used to set the dose and then to inject the set dose. Housing or main body 4 is formed from a lightweight material, such as injection molded plastic. The housing may be molded as a single, tubular piece for robustness. A window 51 in the housing near its proximal end can be filled with a magnifying lens that snaps fits to the housing and allows dosage indicating markings (not explicitly shown) on number sleeve 24 to be readily visible during use. Near the interior distal end of housing 4 is mounted a body part, e.g. a mid-body 20, that is formed with an a central opening having an inward facing anti-rotation mechanism formed from of a pair of diametrically opposed elements or tabs 31 having squared off inward ends that each slidably fit within longitudinal keyways 32 in lead screw 22. In alternate embodiments, features other than tabs and keyways, for instance a lead screw with flats that fits within a complementarily shaped hole in a collar, may be used to prevent rotation. Tabs 31 prevent lead screw 22 from rotating within housing 4 during pen use, but permit lead screw 22 to be shifted longitudinally, such as in the distal direction toward the cartridge. A snap fit or sonic welding connection of the mid-body to the, preferably tubular, housing 4 can be used to prevent axial and rotational relative motion of the mid-body to the housing.

Figure 4:
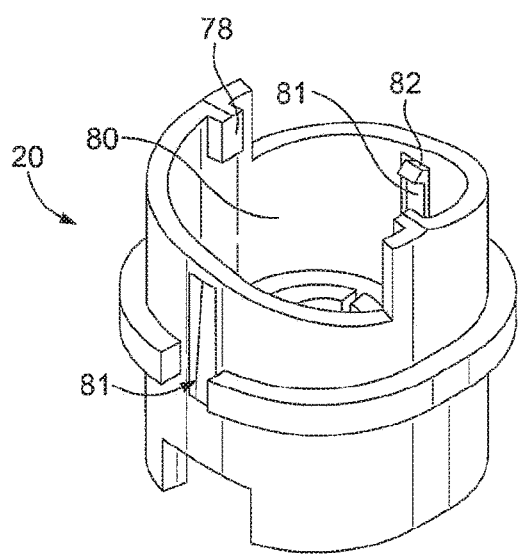
FIG. 4 is a perspective view of one embodiment of a modified mid-body having the second section of the end of dose connection configured as flexible click arms.
Figure 7:
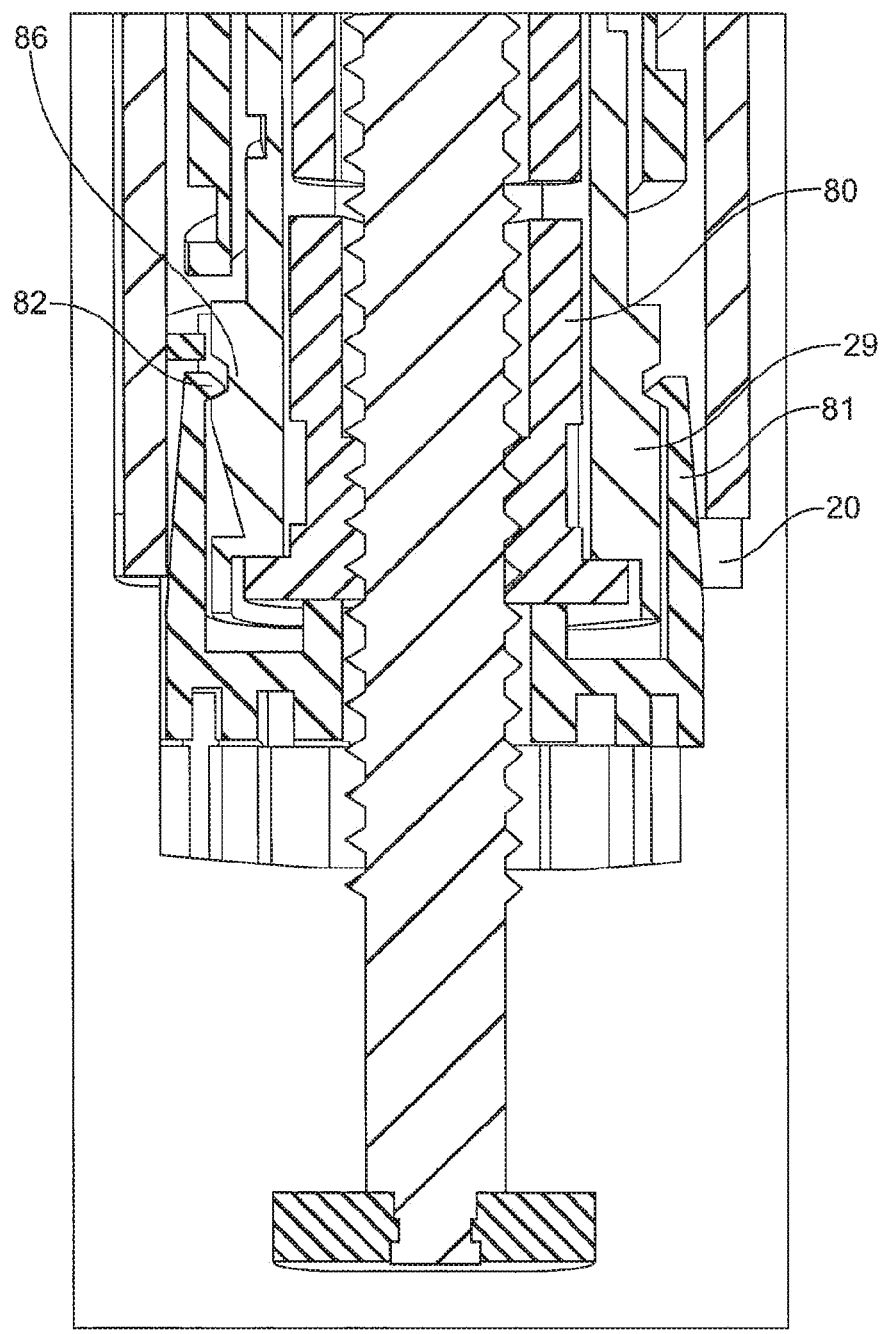
FIG. 7 is a cross sectional view of the distal portion of the dose setting and/or drive mechanism according to one embodiment of the drug delivery device having an end of dose connection as shown in FIGS. 4 and 5.

Mid-body 20 can be modified as illustrated in FIGS. 4 and 7 to include a second section of an end of dose connection that is configured to engage and cooperate with a first section located on the distal portion of inner sleeve 29. As best illustrated in FIG. 4, mid-body 20 has an interior surface 80 that contains one or more flexible click arms 81. Click arm 81 terminates in an inwardly projecting tooth 82 configured for engagement with the first section of the end of dose connection located on the inner sleeve 29. Click arm 81 can be integrally molded with mid-body 20 or can be a separate part either co-molded with or added to the mid-body. Preferably click arm 81 is designed to flex outwardly in a direction transverse to the longitudinal axis of the housing. In a most preferred configuration of the second section of the end of dose connection there are two click arms spaced 180 degrees apart and equidistant from each other on the interior surface of the mid-body. Tooth 82 is configured to interact with a detent, a hole, or an indentetation in the inner sleeve 29 as explained in more detail below and is of a shape to maximize the audible and/or tactile signal generated when the tooth connects with the detent, the hole or the indentation.

Lead screw 22 is in the form of a screw that is axially translatable and rotatably fixed during dosing and injecting. The term "rotatably fixed" shall preferably mean that the lead screw 22 is prevented from rotation during dose setting and dose delivery. Lead screw 22 includes a shaft with a helical threading 33 along its length, which threading is interrupted by longitudinally extending keyways or grooves 32. A thread stop 34 shown at the proximal end of threading 33 is provided and is used in preventing the pen from being set by a user to deliver a dose of medicine larger than remains in cartridge 8. Other forms of stopping the screw motion may be substituted within the scope of the invention, for example, the threading at the proximal screw end could stop near the proximal end where it cannot be cammed in, and such solid screw with thread stop better ensures that the drive nut 23 will not be torqued off the lead screw during dose setting. The distal end of lead screw 22 includes an enlarged, disc-shaped foot or bearing 21 to distribute loading on the cartridge piston 10 that the bearing contacts and thereby directly engages during piston advancing. The separate bearing foot can be attached, such as with a snap fit 20 that may permit relative rotation, to the lead screw. Lead screw 22 is shown as being a one-piece plastic injection molding, but alternate materials of construction and multiple pieces are possible.

Drive nut 23 includes a cylindrical, tube-shaped body with flexible fingers 36 and clicker teeth 35. The distal region of the drive nut 23 is formed with an internal threading 37 that threadedly engages in a friction locking fashion or in a self-locking fashion the threading 33 on lead screw 22. Threadings 33 and 37 are shown as a double start threading but may be differently formed while still providing suitable friction locking capabilities, such as a single start threading or another multiple start threading. Drive nut 23 is located within inner sleeve 29 and is axially, but not rotationally fixed, to the inner sleeve. As drive nut 23 is rotated relative to inner sleeve 29 during dose setting, clicker teeth 35 engage in a ratchet fashion flexible arms 38 that project radially on the inside of inner sleeve 29. As the drive nut rotates the flexible arms ride over teeth 35 creating an audible clicking noise. The teeth are configured so that each click is equal to one dose volume being set. As few as one flexible clicker arm may be provided, but the use of three or four equally angularly spaced arms aids in centering drive nut 23 within the inner sleeve 29. The hollow interior of drive nut body 23 located proximally of threading 37 allows free passage of the proximal end of lead screw 22. The exterior surface of drive nut 23 is designed to cooperatively engage with dial link 25 so that the drive link is axially free and rotatably or rotationally fixed relative to drive nut 23. Thus, during use the dial link is axially movable relative to, but rotatably or rotationally locked with, the threaded drive nut. This connection is possible because of the cooperation of proximally extending fingers 36 on drive nut 23 and the distally extending fingers of dial link 25. These two sets of fingers 36, 43 move axially relative to each other but engage each other rotationally during dose setting when the dial link is rotated by turning dose knob 28, which is fixed to the dial link. Drive nut 23 is shown as being a one-piece plastic injection molding, but other constructions are within the scope of the invention.

In the shown embodiment, dial link 25 is formed in one piece of an injection molded plastic and which fits within body 4. A flange 40 that rings a central region of the dial link body includes splines or teeth 39 that extend from the distal face of flange 40, and teeth 41 that extend from the proximal face of flange 40. A stepped-down portion of the proximal end of dial link 25 forms an axially and proximally extending stem 42. The distal end of the dial link body includes a pair of fingers 43 that fit with fingers 36 of the drive nut 23 to allow axial motion but not rotational motion of the drive nut 23 relative to the dial link 25, thereby rotationally locking the pieces together within the same annular space. Fingers 36 and 43 extend sufficiently axially to ensure they do not disengage during the setting of the maximum pen dose for injection.

An injection molded plastic dose knob 28 with a proximal face, and having a distally facing and centrally located bearing collar and alignment post. Stem 42 of the dial link 25 receives the dose knob alignment post and can be ultrasonically welded within the bearing collar during manufacturing assembly, so as to axially and rotatably or rotationally fix together the dose knob 28 and dial link 25. The term "rotatably fix together" shall preferably mean in this context that any relative rotational movement between the dose knob 28 and the dial link 25 is prevented. Dose knob skirt 50 distally extends from the radial periphery of the dose knob distal face to serve as a grip portion for a user during dose setting.

Coaxially mounted around the dial link 25 is number sleeve 24. Number sleeve 24 has a cylindrical exterior surface 30 with a threading 52 formed as a helical groove that engages a corresponding threading 62 formed on the interior surface of body 4 to threadedly engage the number sleeve 24 to the pen housing. Threadings 52 and 62 are shown as a single start threading but may be differently formed. Threading 62 abuts an end 63 of threading 52 on the number sleeve 24 at the maximum pen dose, assuming the cartridge 8 is sufficiently full for such a maximum dose. A stop surface 64 on the distal end of the outer surface of the number sleeve 24 is positioned in slightly spaced apart relationship with a projecting stop at the zero dose position, and another stop surface is to be abutted by the stop if a user attempts to manually screw the screw element or number sleeve below a zero dose position. A hollow interior 65 of number sleeve 24 is defined by a cylindrical interior surface provided with a helical threading 67.

The outside diameter of number sleeve 24 is selected such that it can fit inside dose knob 28. The proximal end region of number sleeve 24 includes a number of notches 70 and corresponding windows 71 that are alternately spaced around the circumference. Number sleeve 24 includes around its exterior surface 30 suitable indicia of therapeutic dose size as visible through body opening 51. A clutch 26 fits within the open proximal end of number sleeve 24. Ears 72 on the clutch fit within notches 70 and assembly fingers 73 snap lock into windows 71 to axially and rotatably or rotationally lock the number sleeve 24 and the clutch 26 together during manufacturing assembly. A ring of axially extending teeth 54 on the clutch 26 formed in the interior surface of the flange cooperate with the dial link teeth 41 proximally facing on dial link 25. Disposed between the clutch 26 and the inside portion of the dose knob 28 is the spring 27 that urges the clutch to engage teeth 41 on dial link 25. During injection, when a user manually applies a plunging force onto proximal face of dose knob 28, spring 27 is elastically compressed, thus disengaging the clutch 26 and number sleeve 24 from the dial link 25. Flange teeth 41 on dial link and clutch teeth 54 mesh when spring 27 has biased the clutch and attached number sleeve 24 to the dose knob 28 and the dial link 25. Dose knob 28 and dial link 25 are not meshed with clutch 26 and number sleeve 24 when spring 27 has been sufficiently compressed during injecting. While a helically coiled metal wire spring is shown, other forms of commonly known biasing elements may be substituted.

Figure 5:
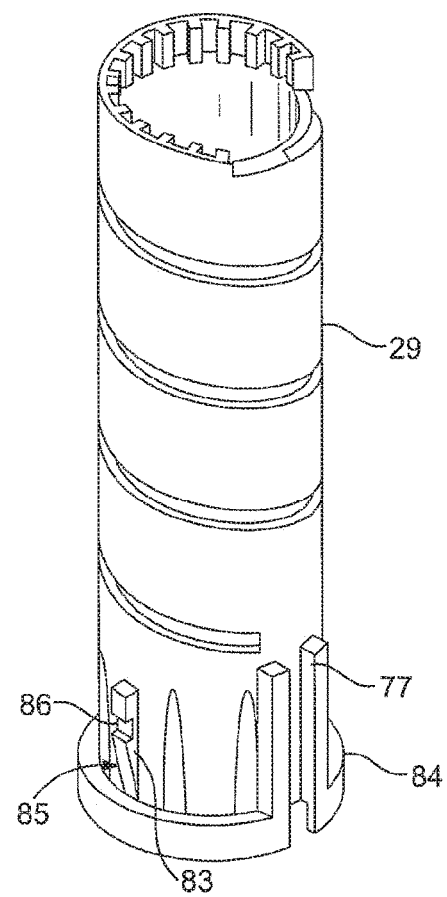
FIG. 5 is a perspective view of one embodiment of a modified inner sleeve having the first section of the end of dose connection configured to engage the mid-body of FIG. 4 through a ramped detent.

Inner sleeve 29 is injection molded from plastic and includes a tubular body that fits into number sleeve hollow 65. The inner sleeve has a helical threading 75 on its outer surface that engages internal threading 67 on inside surface of the number sleeve. Threadings 67 and 75 are shown as a single start threading, but may be differently formed. The most proximal portion of the end of inner sleeve 24, which end is partially helically shaped corresponding to the threading, is notched to form a partial ring of axially projecting teeth 76 that, when meshed with dial link distally facing teeth 39, serve to rotatably or rotationally lock together the dial link and the inner sleeve. Inner sleeve 29 is keyed to pen body 4 through an intermediate mid-body 20 that is axially and rotationally fixed to the body 4. As illustrated in FIG. 5 the distal end or portion 84 of inner sleeve 29 has a pair of ridge-defined slots 77 on the periphery of the inner sleeve which axially, slidably receive the lugs 78 radially inwardly projecting from the mid-body 20. As already mentioned, the distal portion 84 of the inner sleeve 29 contains the first section 83 of an end of dose connection that is formed when the second section 81 located on mid-body 20 is joined to the first section when the drug delivery device is at the zero dose setting or end of injection stroke position. The zero dose setting state of the drug delivery device is when a preset dose of medicament has been fully delivered or expelled from the cartridge by plunging the dose knob and number sleeve distally such that number sleeve is returned to its initial starting position and the dose value viewed through window 51 is zero ("0"). Alternatively, the zero dose setting position can be arrived at if the user dials a dose greater than zero and then decides not to perform an injection and instead dials down or cancels the dose by rotating the dose knob to return the number sleeve to the starting or initial position where the dose value viewed through window 51 is zero ("0").

Figure 6:
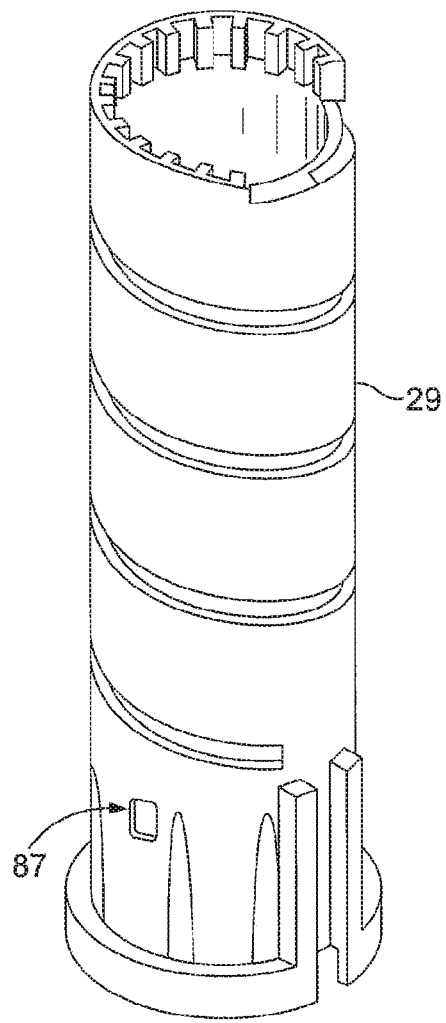
FIG. 6 is a perspective view of another embodiment of a modified inner sleeve having the first section of the end of dose connection configured to engage the mid-body of FIG. 4 through a hole.

The end of dose connection must be reversible and releasable so that after reaching the zero dose setting position the user can dial up a new dose for a subsequent injection. As illustrated in FIGS. 5 and 7 the first section 83 of the end of dose connection on the distal portion of the inner sleeve is configured as a ramped detent having an angled bearing ramp 85 at one end, e.g. the distal end, and a detent notch 86 at the opposite end, e.g. the proximal end. In use, as the inner sleeve is moved axially relative to and inside of the mid-body 20, tooth 82 on click arm 81 rides up the angled bearing ramp 85 until the tooth reaches notch 86 where it then snaps into the notch creating an audible "CLICK" noise that is heard by the user of the drug delivery device. Simultaneously with the "CLICK" there is also a tactile signal that can be felt by the user holding the device. An alternative first section of the end of dose connection is shown in FIG. 6 where the ramped detent is replace by a hole or indentation in the outer surface of inner sleeve 29. It is also within the scope of this invention to reverse the locations of the first and second sections of the end of dose connection.

Openings molded into inner sleeve 29 define four resilient fingers 38 having radially inwardly projecting teeth that are axially oriented and shaped to project into a recess in the distal end of drive nut 23 that has radially projecting teeth or ridges 35 such that the inwardly projecting teeth click over, in either rotational direction, teeth 35 during dose setting. Fingers 38 with teeth cooperate with the recess on the drive nut 23 to hinder the nut from coming off the inner sleeve after being assembled thereto during manufacture.

To facilitate back-driving during dose delivery, the threaded connections of the number sleeve 24 and the body 4, and the number sleeve and the inner sleeve 29, are non-binding and provided by projecting 60° face angle threads that slide within correspondingly designed recessed grooves. With these threadings, it is preferred that the mechanical advantage is 3.4 or greater, and the screw lead of the drive member or drive nut is 0.108 inch.

The operation of the above described embodiment will now be explained. Pen 1 with a needle 16 attached should first be primed to remove any trap air in the cartridge 8 and to ensure the bearing 21 is in contact with the proximal end of the cartridge stopper or piston 10. In particular, typically while clutching the pen body 4 in one hand, a user manually grips dose knob skirt 50 and then begins to turn knob 28 relative to the body 4. At the zero dose arrangement, and as long as knob 28 is not also being plunged which is improper, knob can only be rotated in a dose increasing direction due to the number sleeve not being further movable distally. A user stops the rotating after a short amount of number sleeve travel that is associated with a small delivery volume, such as one or two units, which is indicated by markings visible through window 51. Then, and after removing cap 14 and any other needle cap present, and while pointing the needle tip upward, the user applies a plunging force on dose knob 28 to drive it distally until the number sleeve returns to the zero dose position, at which the number sleeve threading 52 has reached the distal end of the body threading 62, during which plunging action the piston 10 is shifted forward within cartridge 8. If a user sees that the piston movement has caused liquid to reach the needle distal tip, the priming process is complete. If no liquid is visible at needle tip, the priming steps are repeated as needed. After priming, pen 1 is ready to be used for an actual injection.

First, a user prepares the pen by setting the desired dose, as visible in window 51, by turning of knob 28. If the user dials up too large of a dose, and without expelling any medicine, the user can rotate down the dial by turning the knob in the opposite direction, all the way back to zero if desired. To set a dose, the knob is turned in a clockwise direction. Because the dose knob 28 and the dial link 25 are fixed rotationally, the dial link is rotated causing the distally facing fingers 43 to engage the proximally facing fingers 36 of the drive nut 23 to thereby turn the drive nut in same direction. Rotation of the drive nut causes the nut to rotate relative to the stationary lead screw 22 whereby the nut moves or climbs up the lead screw in the proximal direction. The drive nut 23 rotates relative to the inner sleeve 29 that is held rotationally fixed relative to the body 4 through the splined connection to the mid-body. Because drive nut 23 and inner sleeve 29 are axially fixed, proximal axial movement of the drive nut causes the inner sleeve to slide proximally relative to the mid-body 20. Because the clutch 26 is rotationally fixed with the dial link 25 the clutch 26 rotates causing the number sleeve to rotate and to spin out proximally away from body 4. Because the pitch or lead of the threads on the number sleeve are greater than the pitch or lead of the threads on the inner sleeve, the number sleeve and the dial link will translate a larger axial distance compared to the inner sleeve and the drive nut.

To inject the dose, after pen 1 is manipulated so the injection needle distal tip properly penetrates, for example, a user's skin, an axial, distal plunging force is applied to knob face 53 to force the dial link 25 axially in the distal direction towards the body 4, such as with a thumb or index finger of the hand which grasps the housing 4. Initially during injecting, the dial link 25 is shifted axially, which shifting motion compresses the biasing spring 27 to close the gap between the knob surface and the proximal end of the number sleeve 24. The biasing spring is designed to compress prior to the number sleeve moving relative to the body 4. When dial link 25 shifts relative to number sleeve 24 to the axial arrangement of the drive nut 23, clutch teeth 54 and dial link teeth 42 disengage to allow a backdriving rotation of the number sleeve relative to the dial link. During the axial movement of the dial link, drive nut 23 does not move axially or rotationally. When the number sleeve and clutch rotatably or rotationally uncouples from the dial link, as the dial link is continued to be axially plunged without rotation by the user by the plunging of knob 28, the number sleeve 24 screws into the body 4 as it spins relative to knob 28 and the dose markings on the number sleeve that indicate the amount still remaining to be injected is visible through window 51.

As it screws down, number sleeve causes inner sleeve 29 to in essence screw up the internal thread inside of the number sleeve threading as the inner sleeve advances distally a lesser distance than the number sleeve. The advancement of the inner sleeve, due to the abutting or direct engagement with the distal end of the drive nut, advances drive nut without rotation, which due to its threaded connection with the lead screw 22 advances the lead screw axially without rotation, which lead screw advancement shifts cartridge piston 10 to expel medication from the cartridge reservoir. The injection is completed when the number sleeve threading 52 has reached the distal end of the body 4, at which time pen 1 is once again arranged in the ready state or zero dose position.

Pen 1 can continue to be used to deliver any desired dose until the medicine remaining in the cartridge is insufficient for a proper dosing. This insufficiency is indicated to the user by the inability to fully set the desired dose due to drive nut threading 33 abutting thread stop 34 of lead screw 22, at which time the drive nut and dial link cannot be rotated proximally any farther. When insufficient medicine remains, pen 1 may be disposed of and replaced with a similar but entirely new pen. Alternatively, a new cartridge can be provided such that the pen may be reused.

The terms "medicament" or "medicinal product", as used herein, preferably mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative; or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and µ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while µ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ, and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates

While this invention has been shown and described as having various designs, the present invention may be modified within the spirit and scope of this disclosure. For example, to deliver a fixed dose, the pen would preferably be modified such that the maximum that the dial could be screwed out to prepare the pen for injection would correspond to the fixed dose. Such a fixed dose pen could eliminate numerical dosage indicating marking, and instead provide user cues in the form of, for example, instructions and a graphical dosing indicator. This application is therefore intended to cover any variations, uses or adaptations of the invention using its general principles. Further, this application is intended to cover such departures from the present disclosure as come within known or customary practice in the art to which this invention pertains.

The invention claimed is:

1. An assembly for a drug delivery device comprising:
a housing;
a lead screw having a distal end and a proximal end, the lead screw including a threaded shaft;
a drive nut threadedly engaged with and screwable along the threaded shaft;
an inner sleeve which is axially movable and rotatably fixed relative to the housing, wherein the drive nut is axially fixed to the inner sleeve and wherein the inner sleeve has a portion containing a first section of an end of dose feedback connection;
a second section of the end of dose feedback connection which is provided axially fixed within the housing, wherein
the assembly is configured such that, during dose setting, the drive nut is screwed along the threaded shaft, the drive nut carrying with it the inner sleeve,
and wherein
the assembly is configured such that, during dose delivery, the inner sleeve is advanced without rotation to axially advance the drive nut and thereby the lead screw.

2. The assembly of claim 1, wherein the first section of the end of dose feedback connection and the second section of the end of dose feedback connection are configured to cooperate mechanically and, due to this cooperation, to produce an audible and/or tactile signal to indicate that dose delivery has been completed.

3. The assembly of claim 1, further comprising a number sleeve which is threadedly engaged with the housing to be screwable relative to the housing and wherein the inner sleeve is threadedly engaged with the number sleeve.

4. The assembly of claim 3, which comprises a dial link connected with the drive nut and axially movable and rotatably fixed relative to the drive nut, and wherein the dial link is rotatably fixed with the number sleeve when the dial link and the number sleeve are in a first axial arrangement, the number sleeve being rotatable relative to the dial link when the dial link and the number sleeve are in a second axial arrangement.

5. The assembly of claim 1, further comprising a body part which is axially fixed inside of the housing, wherein the inner sleeve is axially movable and rotatably fixed relative to the body part and wherein the body part contains the second section of the end of dose feedback connection.

6. The assembly of claim 1, wherein the drive nut is rotatable with respect to the inner sleeve, and wherein the drive nut and the inner sleeve each comprise one or more corresponding feedback features which are configured to cooperate mechanically such that, when the drive nut rotates relative to the inner sleeve, an audible and/or tactile feedback is generated during the dose setting.

7. The assembly of claim 6, wherein the first section of the end of dose feedback connection and the one or more feedback features of the inner sleeve are arranged in the same portion of the inner sleeve.

8. The assembly of claim 1, wherein the lead screw is rotatably fixed during dose setting and during dose delivery, and wherein the lead screw is axially movable in a distal direction relative to the housing.

9. The assembly of claim 1, wherein the first section of the end of dose feedback connection and the second section of the end of dose feedback connection are configured to establish a releasable connection, the first section and the second section of the end of dose feedback connection being connected before dose setting is commenced, the connection between the first section and the second section of the end of dose feedback connection being released during dose setting and the connection between the first section and the second section of the end of dose feedback connection being re-established at an end of dose delivery.

10. The assembly of claim 1, wherein the first section and second section of the end of dose feedback connection cooperate at a zero dose setting to form a releasable snap fit connection.

11. The assembly of claim 10, wherein the first section and the second section of the end of dose feedback connection are configured to generate an audible sound when the first section and the second section of the end of dose feedback connection cooperate to form the releasable snap fit connection.

12. The assembly of claim 10, wherein the first section and the second section of the end of dose feedback connection are configured to generate a tactile sensation perceptible to a user holding the assembly or the drug delivery device when the first section and the second section of the end of dose feedback connection cooperate to form the releasable snap fit connection.

13. The assembly of claim 1, wherein the first section of the end of dose feedback connection is a flexible click arm and the second section of the end of dose feedback connection is a ramped detent or hole or indentation.

14. The assembly of claim 1, wherein the second section of the end of dose feedback connection comprises at least two click arms and the first section of the end of dose feedback connection comprises at least two ramped detents or two holes or two indentations.

* * * * *